(12) United States Patent
Wang et al.

(10) Patent No.: US 8,551,085 B2
(45) Date of Patent: *Oct. 8, 2013

(54) ABLATION ELECTRODE ASSEMBLY WITH INSULATED DISTAL OUTLET

(75) Inventors: Huisun Wang, Maple Grove, MN (US); Jeremy D. Dando, Plymouth, MN (US); Harry A. Puryear, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1246 days.

This patent is subject to a terminal disclaimer.

(21) Appl. No.: 12/440,866

(22) PCT Filed: Oct. 10, 2007

(86) PCT No.: PCT/US2007/080920
§ 371 (c)(1),
(2), (4) Date: Mar. 11, 2009

(87) PCT Pub. No.: WO2008/045925
PCT Pub. Date: Apr. 17, 2008

(65) Prior Publication Data
US 2009/0259222 A1 Oct. 15, 2009

Related U.S. Application Data

(60) Provisional application No. 60/828,955, filed on Oct. 10, 2006.

(51) Int. Cl.
*A61B 18/14* (2006.01)
(52) U.S. Cl.
USPC .......................................... 606/41
(58) Field of Classification Search
USPC ................................ 606/41; 607/99, 101, 104
See application file for complete search history.

(56) References Cited

U.S. PATENT DOCUMENTS 5,056,517 A 10/1991 Fenici
5,230,349 A 7/1993 Langberg
(Continued)

FOREIGN PATENT DOCUMENTS

EP 0667126 8/1995
WO WO-00/67832 11/2000
(Continued)

OTHER PUBLICATIONS

Wittkampf, Fred H., "Radiofrequency ablation with a cooled porous electrode catheter", *JACC* vol. II, No. 2 Feb. 1988; 17a Feb. 2, 1988.

(Continued)

*Primary Examiner* — Victoria P Shumate
(74) *Attorney, Agent, or Firm* — Dykema Gossett PLLC

(57) ABSTRACT

The present invention relates to improved ablation electrodes (10, 10') and catheter assemblies (12), as well as methods useful in conjunction with irrigated ablation catheters. An irrigated ablation electrode assembly (10, 10') includes a proximal member (18, 18') having an outer surface (22), an inner lumen (26, 26') and a proximal passageway (24). The proximal passageway (24) extends from the inner lumen (26, 26') to the outer surface (22) of the proximal member (18, 18'). The assembly (10, 10') further includes a distal member (20) having a distal end (30) and a distal passageway (28) extending from the inner lumen (26, 26') through the distal member (20) to the distal end (30). Embodiments of the present invention include an irrigated catheter assembly (12) configured to direct irrigation fluid to target areas where coagulation is more likely to occur to, among other things, better minimize blood coagulation and associated problems.

25 Claims, 5 Drawing Sheets

(56) References Cited

U.S. PATENT DOCUMENTS

| | | |
|---|---|---|
| 5,348,554 A | 9/1994 | Imran et al. |
| 5,403,311 A | 4/1995 | Abele et al. |
| 5,423,811 A | 6/1995 | Imran et al. |
| 5,431,168 A | 7/1995 | Webster, Jr. |
| 5,462,521 A | 10/1995 | Brucker et al. |
| 5,545,161 A | 8/1996 | Imran |
| 5,643,197 A | 7/1997 | Brucker et al. |
| 5,676,693 A | 10/1997 | LaFontaine |
| 5,792,140 A | 8/1998 | Tu et al. |
| 5,814,029 A | 9/1998 | Hassett |
| 5,843,152 A | 12/1998 | Tu et al. |
| 5,913,856 A | 6/1999 | Chia et al. |
| 5,919,188 A | 7/1999 | Shearon et al. |
| 5,971,968 A | 10/1999 | Tu et al. |
| 6,017,338 A | 1/2000 | Brucker et al. |
| 6,120,476 A | 9/2000 | Fung et al. |
| 6,141,576 A | 10/2000 | Littmann et al. |
| 6,162,219 A | 12/2000 | Nilsson et al. |
| 6,168,594 B1 | 1/2001 | LaFontaine et al. |
| 6,171,275 B1 | 1/2001 | Webster, Jr. |
| 6,217,576 B1 | 4/2001 | Tu et al. |
| 6,238,393 B1 | 5/2001 | Mulier et al. |
| 6,363,937 B1 | 4/2002 | Hovda et al. |
| 6,383,144 B1 | 5/2002 | Mooney et al. |
| 6,602,242 B1 | 8/2003 | Fung et al. |
| 6,611,699 B2 | 8/2003 | Messing |
| 7,166,105 B2 | 1/2007 | Mulier et al. |
| 7,456,142 B2 | 11/2008 | Hahn |
| 8,034,050 B2 * | 10/2011 | Sharareh et al. .......... 606/41 |
| 2002/0087156 A1 | 7/2002 | Maguire et al. |
| 2003/0212394 A1 | 11/2003 | Pearson et al. |
| 2004/0054272 A1 | 3/2004 | Messing |
| 2005/0090818 A1 * | 4/2005 | Pike et al. .......... 606/41 |
| 2005/0177151 A1 | 8/2005 | Coen et al. |
| 2006/0184165 A1 | 8/2006 | Webster et al. |
| 2006/0264925 A1 * | 11/2006 | Sharareh et al. .......... 606/41 |
| 2007/0156128 A1 * | 7/2007 | Jimenez .......... 606/34 |
| 2007/0156131 A1 | 7/2007 | Datta |
| 2007/0270791 A1 | 11/2007 | Wang et al. |
| 2009/0177193 A1 | 7/2009 | Wang et al. |

FOREIGN PATENT DOCUMENTS

| | | |
|---|---|---|
| WO | WO-2005/048858 | 6/2005 |
| WO | WO 2005/048858 A1 | 6/2005 |
| WO | WO 2005/112814 A2 | 12/2005 |
| WO | WO 2007/136979 A2 | 11/2007 |
| WO | WO 2008/045925 A3 | 4/2008 |

OTHER PUBLICATIONS

Wittkampf, Fred et al., "Saline-Irrigated Radiofrequency ablation electrode with external cooling", *Journal of Cardiovascular Electrophysiology*, vol. 16 Mar. 3, 2005.

Smith, Tennyson, et al., "The Hydrophilic Nature of a Clean Gold Surface", *Journal of Colloid and Interface Science*, vol. 75, No. 1 May 1, 1980, 51-55.

* cited by examiner

ABLATION ELECTRODE ASSEMBLY WITH INSULATED DISTAL OUTLET

CROSS-REFERENCE TO RELATED APPLICATIONS

This application claims the benefit of U.S. provisional application No. 60/828,955, filed 10 Oct. 2006, which is hereby incorporated by reference as though fully set forth herein.

BACKGROUND OF THE INVENTION

A. Field of the Invention

The present invention relates to irrigated catheter assemblies. The present invention further relates to ablation electrodes and assemblies, including electrode assemblies having distal irrigation fluid flow. The present invention further relates to ablation electrode assemblies having at least one temperature sensing device and a mechanism for irrigating the ablation assembly and targeted areas. The present invention further relates to methods for improved assembly and accurate measurement and control of the electrode temperatures while effectively irrigating the device and target areas.

B. Background Art

Electrophysiology catheters are used for an ever-growing number of procedures. Catheters are used for diagnostic, therapeutic, and ablative procedures, to name just a few examples. Typically, a catheter is manipulated through the patient's vasculature and to the intended site, for example, a site within the patient's heart. The catheter typically carries one or more electrodes, which may be used for ablation, diagnosis, or other treatments.

There are a number of methods used for ablation of desired areas, including for example, radiofrequency (RF) ablation. Ablation may be facilitated by transmission of energy from an electrode assembly to ablate tissue at the target site. Because ablation may generate significant heat, which if not controlled can result in excessive tissue damage, such as steam pop, tissue charring, and the like, it is desirable to include a mechanism to irrigate the target area and the device with biocompatible fluids, such as water or saline solution. The use of irrigated ablation catheters can also prevent the formation of soft thrombus and/or blood coagulation.

Typically, there are two classes of irrigated electrode catheters, open and closed irrigation catheters. Closed ablation catheters usually circulate a cooling fluid within the inner cavity or lumen provided by the ablation electrode. Open ablation catheters typically deliver the cooling fluid through open outlets or openings to a surface of the electrode. Open ablation catheters use an inner cavity or lumen of the electrode, as a manifold to distribute saline solution, or other irrigation fluids known to those skilled in the art, to one or more passageways that lead to an opening/outlet provided on the surface of the electrode. The cooling fluid thus flows through the outlets of the passageways onto the electrode member. This flow through the electrode tip lowers the temperature of the tip during operation, often making accurate monitoring and control of the ablative process more difficult.

In general, open irrigated ablation catheters may improve the function and safety associated with catheter ablation by preventing protein aggregation and blood coagulation. A particular area of the electrode/catheter where the formation of coagulum or thrombus may occur during ablation procedures is at the distal end or tip of the electrode.

BRIEF SUMMARY OF THE INVENTION

The present invention is directed to improved ablation electrode assemblies and methods useful in conjunction with irrigated catheter devices and other ablation catheters. Embodiments of the present invention provide an irrigated catheter having irrigation fluid directed at target areas where coagulation is more likely to occur so as to minimize blood coagulation and associated problems. The present invention includes various embodiments of irrigation electrode assemblies having a passageway for minimizing the blood coagulation and related problems occurring at or about the distal end of the electrode.

Accordingly, the present invention includes an irrigated ablation electrode assembly. The electrode assembly includes a proximal member having an outer surface and an inner lumen. The electrode assembly further includes a distal member having an outer surface and a distal end. The proximal member and distal member are configured for connection with one another. The assembly further includes at least one proximal passageway extending from the inner lumen to the outer surface of the proximal member. The assembly further includes a distal passageway extending from the inner lumen through the distal member to the distal end of the electrode assembly. In an embodiment, the proximal passageway is separated from and does not come in contact with the distal member.

The present invention further includes an alternate embodiment of an irrigated ablation electrode assembly. In an alternate embodiment, the electrode assembly includes a proximal member having an outer surface and an inner lumen. The electrode assembly further includes a distal member having an outer surface and a distal end. The proximal member and distal member are configured for connection with one another. The assembly further includes at least one proximal passageway extending from the inner lumen to the outer surface of the proximal member. The assembly further includes a distal passageway extending from the inner lumen through the distal member to the distal end of the electrode assembly. According to the alternate embodiment, the proximal member has a lower thermal conductivity than the distal member.

The present invention further includes an alternate embodiment of an irrigated ablation electrode assembly. In an alternate embodiment, the electrode assembly includes a proximal member having an outer surface and an inner lumen. The electrode assembly further includes a distal member having an outer surface and a distal end. The proximal member and distal member are configured for connection with one another. The assembly further includes at least one proximal passageway extending from the inner lumen to the outer surface of the proximal member. The assembly further includes a distal passageway extending from the inner lumen through the distal member to the distal end of the electrode assembly. The assembly further includes an insulating member at least partially separating the distal passageway from the distal member, wherein the insulating member has a lower thermal conductivity than the distal member.

The present invention further includes an alternate embodiment of an irrigated ablation electrode assembly. In an alternate embodiment, the electrode assembly includes a proximal member having an outer surface and an inner lumen. The electrode assembly further includes a distal member having an outer surface and a distal end. The proximal member and distal member are configured for connection with one another. The assembly further includes at least one proximal passageway extending from the inner lumen to the outer surface of the proximal member. The assembly further includes a distal passageway extending from the inner lumen through the distal member to the distal end of the electrode assembly. In accordance with an alternate embodiment, the inner lumen includes a hydrophilic coating.

The foregoing and other aspects, features, details, utilities, and advantages of the present invention will be apparent from reading the following description and claims, and from reviewing the accompanying drawings.

DETAILED DESCRIPTION OF THE INVENTION

In general, the instant invention relates to irrigated ablation electrode assemblies, to catheter assemblies, as well as ablation systems employing the irrigated ablation electrode assemblies, 10 and 10', in connection with catheter assemblies. For purposes of this description, similar aspects among the various embodiments described herein will be referred to by the same reference number. As will be appreciated, however, the structure of the various aspects may differ with respect to alternate embodiments.

Figure 1:
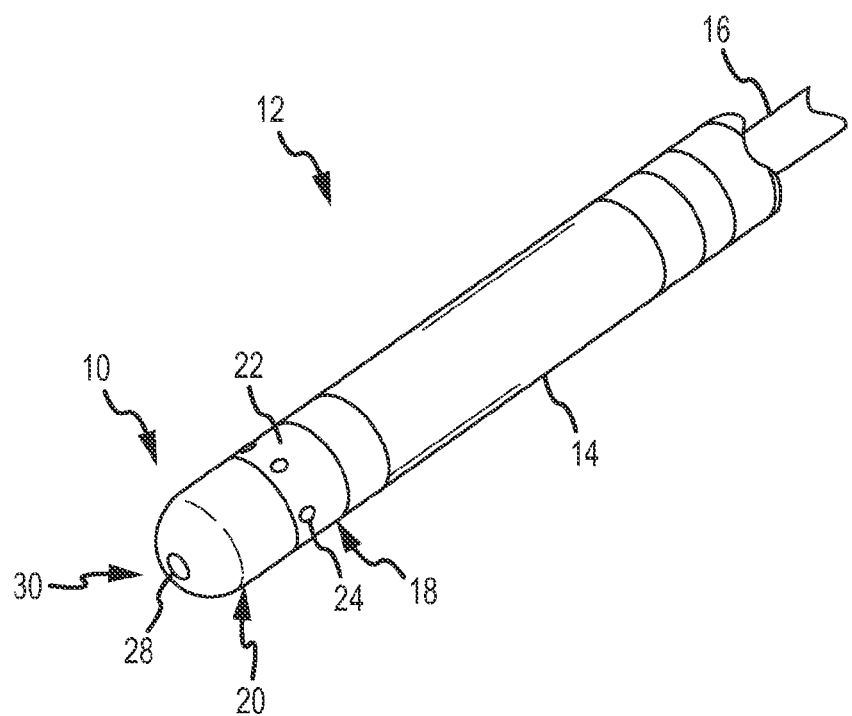
FIG. 1 is an isometric view of an ablation electrode according to an embodiment of the present invention.

As generally shown in the embodiment illustrated in FIG. 1, the ablation electrode assembly 10 may comprise part of an irrigated ablation catheter assembly 12. The embodiments describe RF ablation electrodes and assemblies, but it is contemplated that the present invention is equally applicable to any number of other ablation electrodes and assemblies where the temperature of the device and the targeted tissue area may be factors during the procedure. FIGS. 3-8 as discussed in more detail below, illustrate ablation electrode assemblies 10, 10' according to alternate embodiments of the present invention.

Figure 2:
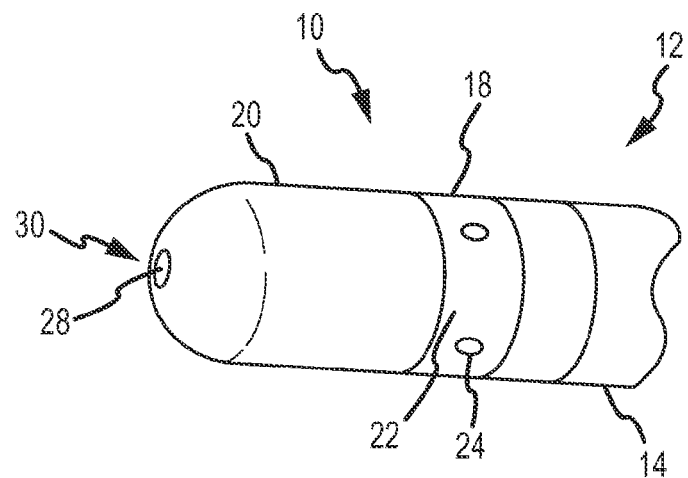
FIG. 2 is an enlarged isometric view of the distal end of the ablation electrode as shown in FIG. 1.
Figure 5:
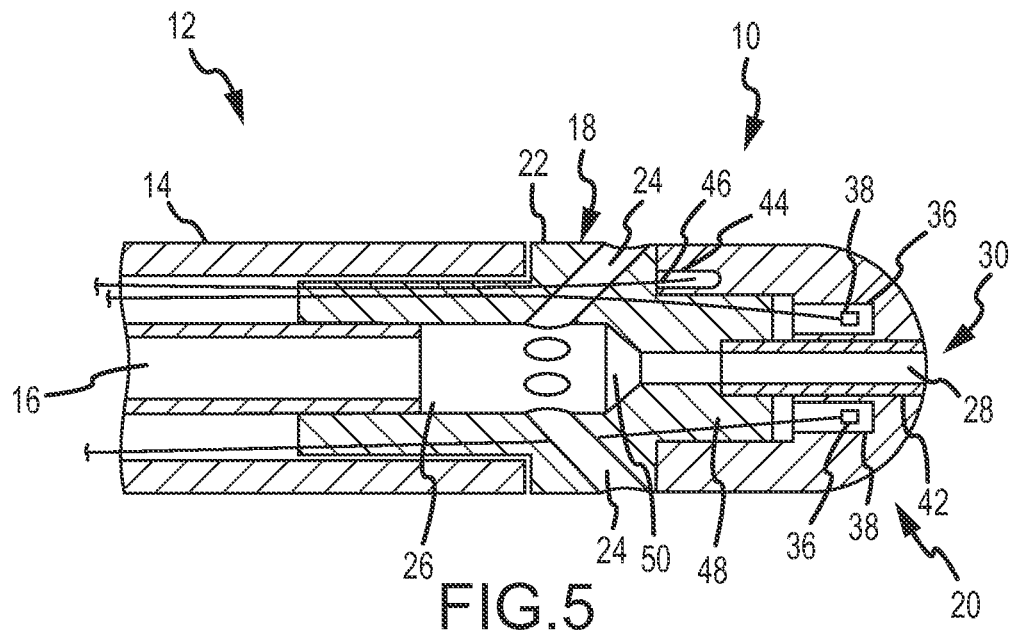
FIGS. 5-7 are side cross-sectional views of ablation electrodes according to alternate embodiments of the present invention.
Figure 6:
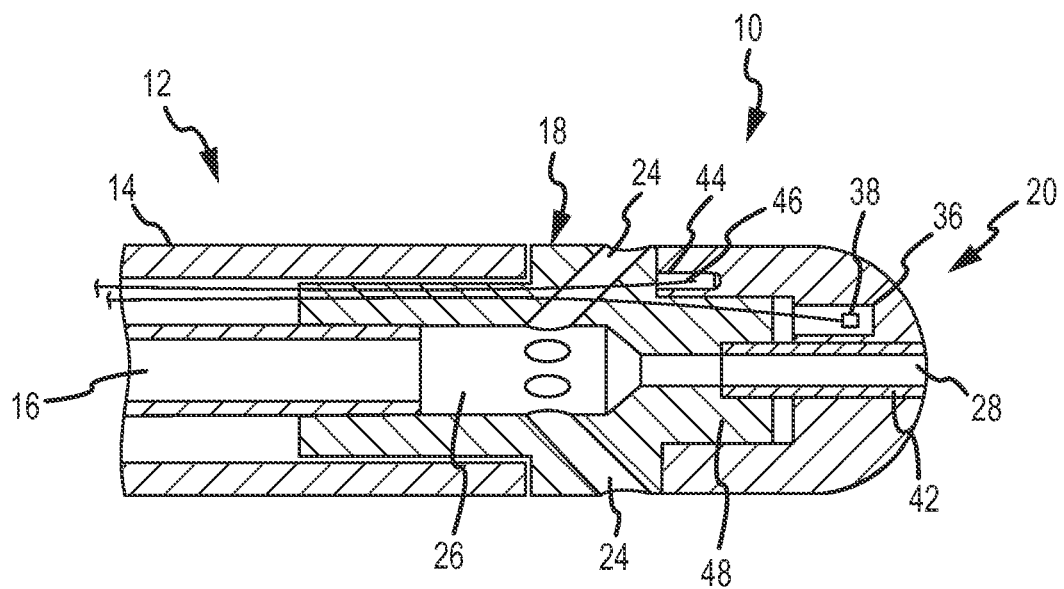
Figure 7:
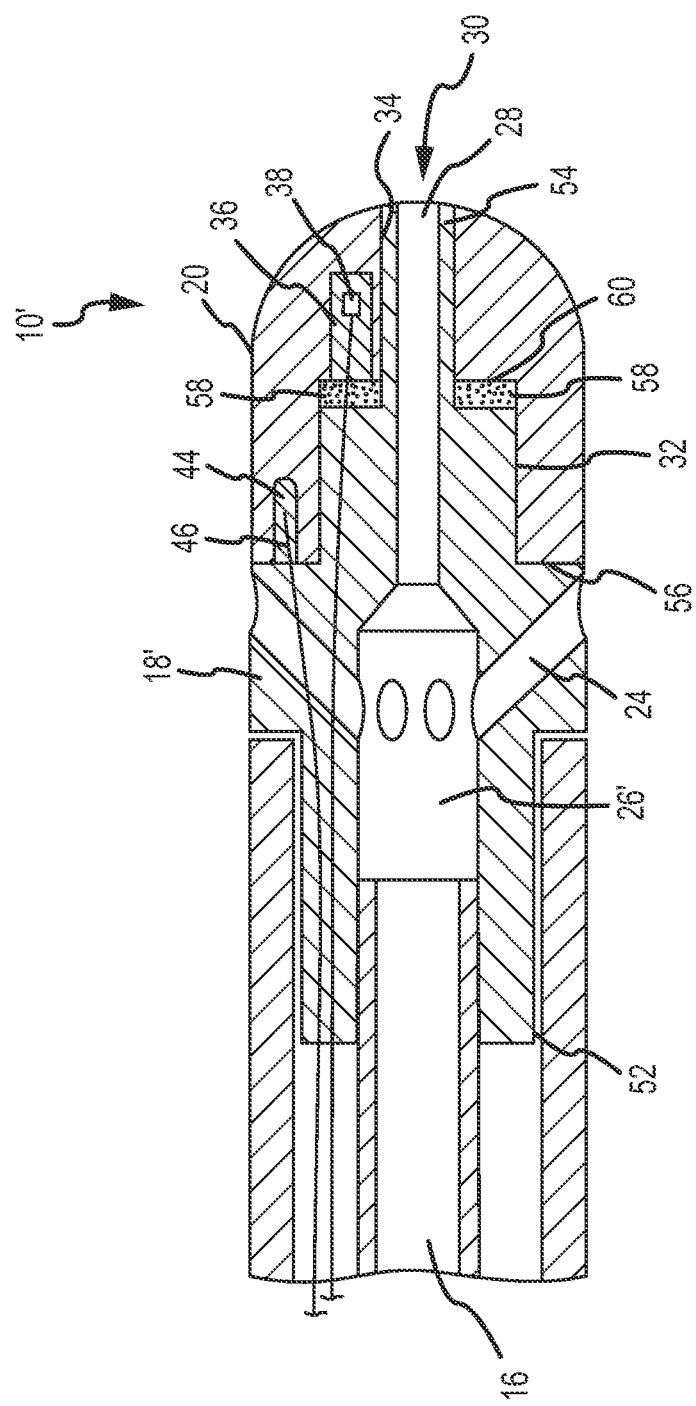

In accordance with an embodiment, FIG. 1 generally illustrates an ablation electrode assembly 10 connected to catheter shaft 14 as part of irrigated ablation catheter assembly 12. The assembly 12 includes at least one fluid delivery tube 16. Ablation electrode assembly 10 includes a proximal member 18, also referred to as an irrigation member or manifold, and a distal member 20, also referred to as an ablation electrode member. Proximal member 18 and distal member 20 are configured to be connected together. The orientation of members 18, 20 are generally such that distal member 20, which provides an ablation electrode or an ablative surface, is situated at the distal end of assembly 10. Proximal member 18, or irrigation member, is located at the proximal end of assembly 10, although for some embodiments the orientation could be reversed. Proximal member 18 includes an outer surface 22. Proximal member 18 further includes at least one fluid or irrigation passageway 24, also referred to as proximal passageway 24, that extends from an inner lumen 26, for example as generally shown in FIGS. 5-7, to outer surface 22 of proximal member 18. Inner lumen 26 is in fluid communication with fluid delivery tube 16. As can be further seen in FIGS. 2-4, distal member 20 includes a distal passageway 28 that extends to distal end 30 of electrode assembly 10. Fluid passageways 24 of proximal member 18 and distal passageway 28 allow for increased irrigation of electrode assembly 10 during the ablation of tissue. Proximal passageway 24 is separated from and does not come in contact with distal member 20.

Figure 3:
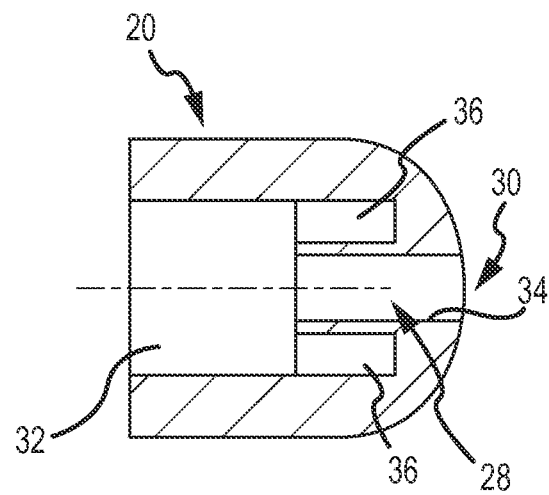
FIG. 3 is a side cross-sectional view of a distal member of an ablation electrode according to an alternate embodiment of the present invention.
Figure 4:
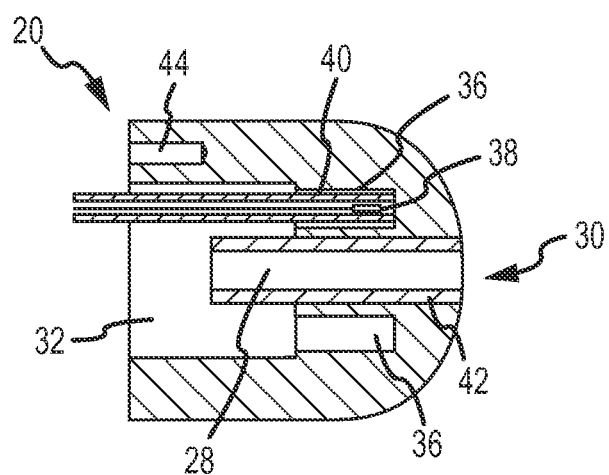
FIG. 4 is a side cross-sectional view of a distal member of an ablation electrode according to an alternate embodiment of the present invention.

Distal member 20, as shown in FIGS. 3 and 4, is generally comprised of an electrically, and potentially thermally, conductive material known to those of ordinary skill in the art for delivery of ablative energy to target tissue areas. Examples of electrically conductive material include gold, platinum, iridium, palladium, stainless steel, and various mixtures and combinations thereof. In an embodiment, the distal member may be hemispherical or semispherical in shape, although other configurations may be used.

Distal member 20 may further include an inner cavity 32 for receiving a portion of proximal member 18, as further discussed below. Distal member 20 further includes an aperture 34 therein forming distal passageway 28. Aperture 34 extends through distal member 20 to distal end 30 therein providing an opening or outlet for distal passageway 28 on the surface of distal member 20. Distal member 20 may further be configured with one or more component cavities 36 for receiving and/or housing additional components within distal member 20.

As can be seen in FIG. 4, at least one temperature sensor 38, also referred to as a temperature or thermal sensing device, may be provided within a portion (e.g., cavity 36) of distal member 20. In an alternate embodiment, two temperature sensors may be provided within cavities 36 of distal member 20. Various configurations of distal member 20 may include temperature sensor 38 in different locations and proximities within distal member 20. In an alternate embodiment, the temperature sensor 38 may be either partially or completely surrounded by or encapsulated by an insulation liner 40 that is made of thermally conductive and electrically non-conductive materials. Insulation liner 40 may be provided in various configurations, such as provided by a tube-like configuration, as shown in FIG. 4. Liner 40 may be comprised of various materials, such as for example polyimide tubing.

As generally illustrated in FIG. 4, distal member 20, may further include an insulating member 42, i.e. thermal liner, disposed within aperture 34, forming distal passageway 28 of distal member 20. Insulating member 42 may be comprised of a non and/or poor thermally conductive material. Such material may include, but is not limited to, high-density polyethylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof. Insulating member 42 may be generally provided in a configuration that reflects the size and shape of aperture 34, although the insulating member 42 generally extends to meet and connect to inner lumen 26 of proximal member 18. Distal passageway 28 is therein created for the flow of fluid from proximal member 18, for example, as generally shown in FIGS. 5-7, through distal passageway 28 to distal end 30 of assembly 10.

An alternate embodiment of distal member 20 includes a cavity 44 for receiving a power wire 46 (see, e.g., FIGS. 5-7) for connecting distal member 20 to an energy source, such as an RF energy source. In an alternate embodiment, cavity 44 may further include a non and/or poor thermally conductive material. Furthermore, in an alternate embodiment, power wire 46 may be soldered directly to distal member 20, or attached and/or connected to distal member 20 through the use of an adhesive or any other connection method known to one of ordinary skill in the art.

FIGS. 5-7 generally illustrate alternate embodiments of electrode assembly 10, 10' of the present invention. As previously described, proximal member 18, 18' and distal member 20 are configured to be connected and/or coupled together with one another. Proximal member 18, 18' is comprised of a thermally nonconductive or reduced (i.e. poor) thermally conductive material that serves to insulate the fluid from the remaining portions of electrode assembly 10, in particular distal member 20. Moreover, proximal member 18, 18' may comprise an electrically nonconductive material. Comparatively, overall, proximal member 18, 18' may have lower thermal conductivity than distal member 20. In an embodiment, proximal member 18, 18' is made from a reduced thermally conductive polymer. A reduced thermally conductive material is one with physical attributes that decrease heat transfer by about 10% or more, provided that the remaining structural components are selected with the appropriate characteristics and sensitivities to maintain adequate monitoring and control of the process. One reduced thermally conductive material may include polyether ether ketone ("PEEK"). Further examples of reduced thermally conductive materials useful in conjunction with the present invention include, but are not limited to, high-density polytheylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof. Moreover, proximal member 18 is substantially less thermally conductive than distal member 20. As a result, the irrigation fluid flowing through proximal member 18 has very little thermal effect on distal member 20 due to the poor thermal conductivity of proximal member 18 (e.g. less than 5% effect), and preferably nearly 0% effect. In general, characteristics and descriptions (e.g. composition and materials) regarding proximal member 18 and 18' may be used interchangeably, among various embodiments except for the specific descriptions provided regarding the design of proximal member 18' in accordance with the embodiment provided in FIG. 7.

The proximal member 18 may further be configured to include a coupling portion 48 that extends into inner cavity 32 of distal member 20. Proximal member 18 may be generally cylindrical in shape. Moreover, for some embodiments, distal member 20 of ablation electrode assembly 10 may have a generally cylindrical shape terminating in a hemispherical distal end 30. The cylindrical shape of proximal member 18 and distal member 20 may be substantially similar to one another and generally have the same overall diameter, which can provide or create a smooth outer body or profile for electrode assembly 10. Distal member 20 may be configured to accept portion 48 of proximal member 18 for attachment thereto. The distal member 20 may be connected by any known mechanism including adhesives, press-fit configurations, snap-fit configurations, threaded configurations, or any other mechanism known to one of ordinary skill in the art.

Proximal member 18 may further include an inner lumen 26 that is connected to fluid delivery tube 16. The inner lumen 26 may act as a manifold or distributor for transporting and/or distributing fluid throughout electrode assembly 10. In particular, proximal member 18 may be configured to receive a fluid delivery tube 16 carried within at least a portion of catheter assembly 12. Proximal member 18 includes a plurality of passageways 24. Proximal member 18 may serve as a manifold or distributor of fluid to electrode assembly 10 through the use of passageways 24. Proximal passageways 24 may extend from inner lumen 26 axially toward outer surface 22 of proximal member 18. In an embodiment, a plurality of passageways 24 are substantially equally distributed around proximal member 18 to provide substantially equal distribution of fluid to the targeted tissue area and/or the outside of electrode assembly 10. Electrode assembly 10 may be configured to provide a single, annular passageway 24, or a number of individual passageways 24 equally distributed around the proximal member 18. Moreover, the passageways 24 may be generally tubular and may have a constant diameter along the length of the passageway. Alternate configurations having various diameters along all or portions of the length of the passageways may be used.

As shown in FIGS. 5-7, proximal passageways 24 may be directed towards or extend towards distal member 20 of electrode assembly 10 at an angle (Θ) less than 90 degrees from the central longitudinal axis of proximal member 18. In an embodiment, passageways 24 extends at an angle (Θ) between about 20 to about 70 degrees, and for some embodiments, between about 30 to about 60 degrees. Alternate positions and angles of the passageway(s) 24 may be provided in alternate embodiments of electrode assembly 10.

Distal passageway 28 is provided for and extends along the central longitudinal axis of proximal member 18 through distal member 20 to distal end 30 of electrode assembly 10. As shown in FIGS. 5 and 6, distal passageway 28 may further be fully or partially surrounded by a thermally non-conductive material, such as that provided by insulating member 42. Insulating member 42 prevents saline or any other biocompatible fluid from coming in contact with distal member 20. Insulating member 42 may be comprised of a thermally nonconductive material such as, but not limited to, high-density polyethylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof.

Distal passageway 28 extends from inner lumen 26 provided by proximal member 18. In general, the diameter of distal passageway 28 is less than the diameter of inner lumen 26 of proximal member 18. Accordingly, in one embodiment, inner lumen 26 and distal passageway 28 may be connected by a tapered transition portion 50 therein providing constant fluid communication. The angle of the tapered transition portion may vary depending on the diameters of the inner lumen 26 and distal passageway 28, as well as the length of proximal member 18. The presence of the tapered transition portion 50 between inner lumen 26 and distal passageway 28 prevents air bubbles from being trapped inside the proximal member during fluid flow through the lumen and passageways. In an embodiment, distal passageway 28 is slightly larger in diameter than passageways 24 provided by the proximal member. The diameter of passageways 24 and distal passageways 28 may vary depending on the configuration and design of electrode assembly 10. In an embodiment, distal passageway 28 includes a diameter within the range of about 0.012 to about 0.015 inches, more particularly about 0.013 to about 0.014 inches. In another embodiment, proximal passageways 24 include a diameter within in the range of about 0.011 to about 0.014 inches, more particularly about 0.011 to about 0.013 inches.

In another embodiment, the inner surface of inner lumen 26 may be either coated with a hydrophilic coating or surface treated to create a hydrophilic surface. The treatment of inner lumen 26 with a hypdrophilic surface or coating results in another method of preventing air bubbles from becoming trapped inside proximal member 18. The hydrophilic coating materials may include, but are not limited to, block copolymers based of ethylene oxide and propylene oxide, polymers in the polyethylene glycol family and silicone. For example, those materials selected from the group including PLURONIC® from BASF, CARBOWAX® from Dow Chemical Company and SILASTIC MDX® from Dow Corning.

Alternate embodiments of the present invention provide the incorporation of at least one temperature sensor 38 in combination with distal passageway 28. In particular, an embodiment, as shown in FIG. 5, includes two temperature sensors 38 provided within cavities 36 of distal member 20. In an alternate embodiment, as shown in FIG. 6, one temperature sensor is provided within a single cavity 36. Temperature sensors may include various temperature sensing mechanisms, such as a thermal sensor, disposed therein for measurement and control of electrode assembly 10. The temperature sensor 38 can be any mechanism known to one of skill in the art, including for example, thermocouples or thermistors. The temperature sensor 38 may further be surrounded, or encapsulated, by a thermally conductive and electrically non-conductive material, as previously discussed. This thermally conductive and electrically non-conductive material can serve to hold temperature sensor 38 in place within distal member 20 and provide improved heat exchange between temperature sensor 38 and distal member 20. This material may be comprised of a number of materials known to one of ordinary skill in the art, including for example, thermally conductive resins, epoxies, or potting compounds.

In another embodiment of electrode assembly 10, as seen in FIG. 7, proximal member 18' includes proximal end 52 and an extended distal end 54 that is received within aperture 34 of distal member 20 when proximal member 18' and distal member 20 are configured for connection. Distal member 20 provides a proximal surface 56 and well the surface 60 provided by inner cavity 32 that may be connected to proximal member 18' through the use of bonding or adhesive 58, therein coupling and/or connecting proximal member 18' with distal member 20. Inner lumen 26' extends from proximal end 52 to distal end 54 of proximal member 18'. Accordingly proximal member 18 is configured to provide the insulating portion of distal passageway 28 through distal member 20. As a result, the non-thermally conductive material of the proximal member, as previously described above, insulates distal passageway 28 through distal member 20. Proximal member 18' further includes proximal passageways 24, as described above that allow fluid flow from inner lumen 26' to outer surface 22' of proximal member 18'. Passageways 24 are directed towards distal member 20 to increase the fluid flow around the intersection of the proximal member to the distal member.

Figure 8:
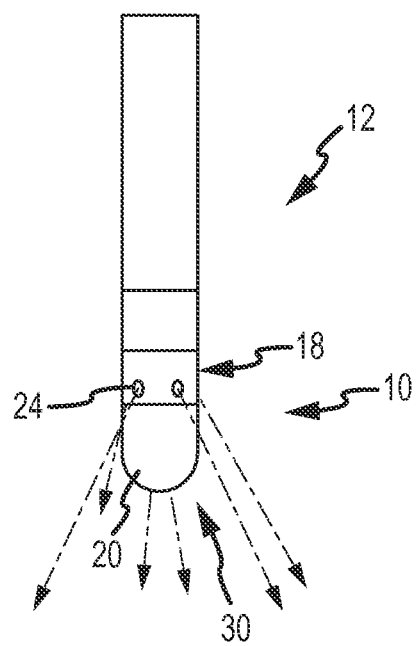
FIG. 8 is an illustrative view of visualized irrigation flow from an ablation electrode according to an alternate embodiment of the present invention.

The flow of fluid through inner lumen 26' provided by fluid tube 16 and ultimately through proximal passageways 24 and distal passageway 28 is reflected in FIG. 7. In particular, FIG. 8 provides an irrigation flow visualization wherein the fluid from proximal passageways 24 is directed at a 30 degree angle from the central longitudinal axis of proximal member 18, as shown in FIG. 7. The flow visualization further shows the flow of fluid out of distal passageway 28, as shown in FIGS. 5-7, from distal end 30 of electrode assembly 10'.

Figure 9:
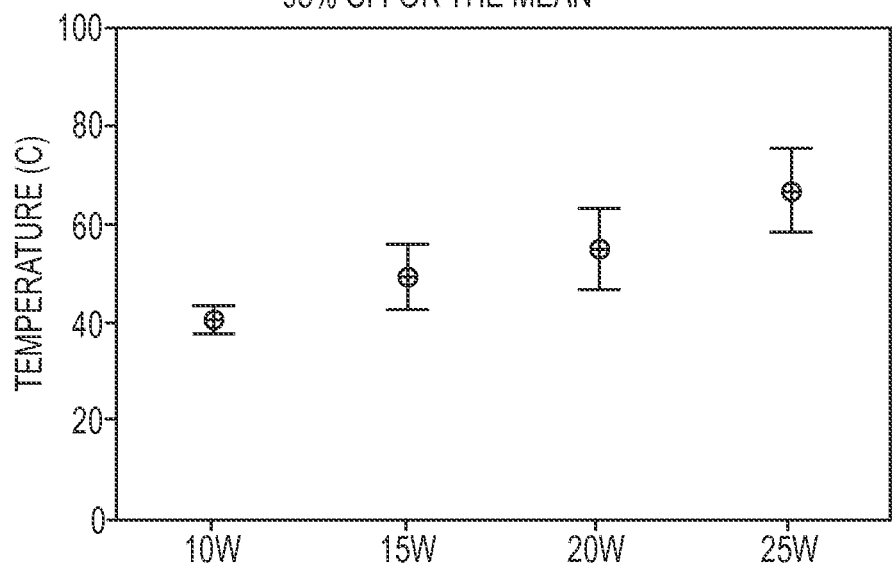
FIG. 9 graphically depicts general bench test results for ablation electrode assemblies in accordance with an embodiment of the present invention.

FIG. 9 graphically depicts bench test results for ablation electrode assemblies in accordance with an embodiment of the present invention. The purpose of the testing was to confirm that adequate temperature control was being accomplished through the use of the irrigated electrode including a distal passageway as the ablation system was subjected to an overall increase in power (W) (e.g. wattage). Overall, the testing was performed using an embodiment of the present invention wherein ablation was being performed using an electrode assembly that maintained irrigation flow of fluid was 13 mL/M at a perpendicular orientation to the muscle tissue being ablated. The testing showed, as reflected in FIG. 9, that an adequate temperature response was exhibited by the ablation electrode assembly, upon the continued increase of power (W) provided to the ablation system. Overall, the ablation electrode, as provided by the present invention, having a distal irrigation passageway was able to maintain adequate temperature control, for performing ablation, while at the same time sufficiently cooling the electrode tip. Accordingly, it is desirable to provide an irrigated ablation electrode assembly in accordance with the present invention that can achieve adequate temperature response within a desired range for performing ablation procedures.

As previously discussed, the ablation electrode assembly 10, 10' of the present invention may comprise part of an irrigated ablation catheter assembly 12, operably connected to a pump assembly and an RF generator assembly which serves to facilitate the operation of ablation procedures through monitoring any number of chosen variables (e.g. temperature of the ablation electrode, ablation energy, and position of the assembly), assist in manipulation of the assembly during use, and provide the requisite energy source delivered to the electrode assembly 10, 10'. Although the present embodiments describe RF ablation electrode assemblies and methods, it is contemplated that the present invention is equally applicable to any number of other ablation electrode assemblies where the temperature of the device and the targeted tissue areas is a factor during the procedure.

In addition to the preferred embodiments discussed above, the present invention contemplates methods for improved measure and control of a temperature of an irrigated ablation electrode assembly 10, 10' or a target site and minimization of coagulation and excess tissue damage at and around the target site. According to one method, an ablation electrode assembly 10, 10' is provided, having at least one temperature sensor 38 within distal member 20 and proximal member 18 is separate from distal member 20. An irrigation pathway 24 is provided within the proximal member 18 for delivery of fluid to the outer surface 22 of the proximal member 18. A distal passageway 28 is further provided for delivery of fluid to the distal end of distal member 20, thereby allowing for the benefits of irrigation of the target site and external portions of electrode assembly 10, such as minimizing tissue damage, such as steam pop, preventing rising impedance of the ablation assembly, and minimizing blood coagulation.

Other embodiments and uses of the devices and methods of the present invention will be apparent to those skilled in the art from consideration of the specification and practice of the invention disclosed herein. The specification and examples should be considered exemplary only with the true scope and spirit of the invention indicated by the following claims. Although a number of embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An irrigated ablation electrode assembly comprising:
a proximal member having an outer surface, an inner lumen and a proximal fluid passageway extending from the inner lumen to the outer surface of the proximal member; and
a distal member having an outer surface, a distal end, and a distal fluid passageway extending from the inner lumen through the distal member to the distal end;
wherein the proximal member and distal member are configured for connection with one another, and the proximal fluid passageway does not contact the distal member.

2. The electrode assembly of claim 1, including a temperature sensor in the distal member.

3. The electrode assembly of claim 2, wherein at least a portion of the temperature sensor is surrounded by an electrically nonconductive material.

4. The electrode assembly of claim 1, wherein the proximal member is substantially less thermally conductive than the distal member.

5. The electrode assembly of claim 1, wherein the proximal member is comprised of an electrically nonconductive material and the distal member is comprised of an electrically conductive material.

6. The electrode assembly of claim 1, wherein at least a portion of the distal fluid passageway is thermally insulated from the distal member by a thermally nonconductive material.

7. The electrode assembly of claim 1, wherein the distal fluid passageway extends axially along a central longitudinal axis of the proximal member towards the distal member.

8. The electrode assembly of claim 1, wherein the proximal fluid passageway extends towards the distal member at an angle less than perpendicular to a central longitudinal axis of the proximal member.

9. The electrode assembly of claim 8, wherein the proximal fluid passageway extends towards the distal member at an angle between about 20 and about 70 degrees from an angle perpendicular to the central longitudinal axis of the outer body portion of the assembly.

10. The electrode assembly of claim 1, wherein the diameter of the inner lumen is greater than the diameter of the distal fluid passageway and are connected together by a tapered transition portion of the inner lumen.

11. The electrode assembly of claim 1, wherein the inner lumen includes a hydrophilic coating.

12. An irrigated ablation electrode assembly comprising:
a proximal member having an outer surface, an inner lumen and a proximal fluid passageway extending from the inner lumen to the outer surface of the proximal member; and
a distal member having an outer surface, a distal end, and a distal fluid passageway extending from the inner lumen through the distal member to the distal end;
wherein the proximal member and distal member are configured for connection with one another, and the proximal member has a lower thermal conductivity than the distal member.

13. The electrode assembly of claim 12, including a temperature sensor in the distal member.

14. The electrode assembly of claim 12, wherein the proximal member is comprised of an electrically nonconductive material and the distal member is comprised of an electrically conductive material.

15. The electrode assembly of claim 12, wherein the diameter of the inner lumen is greater than the diameter of the distal fluid passageway and are connected together by a tapered transition portion of the inner lumen.

16. The electrode assembly of claim 12, wherein the proximal fluid passageway extends towards the distal member at an angle less than perpendicular to a central longitudinal axis of the proximal member.

17. An irrigated ablation catheter comprising:
a catheter shaft having a distal end;
a proximal member connected to the distal end of the catheter shaft, the proximal member having an outer surface, an inner lumen, and a proximal fluid passageway extending from the inner lumen to the outer surface of the proximal member; and
a distal member connected to the proximal member, the distal member having an outer surface, a distal end, and a distal fluid passageway extending from the inner lumen through the distal member to the distal end;
wherein the proximal member has a lower thermal conductivity than the distal member, and the distal member comprises an electrode.

18. An irrigated ablation electrode assembly comprising:
a proximal member having an outer surface, an inner lumen and a proximal passageway extending from the inner lumen to the outer surface of the proximal member,
a distal member having an outer surface, a distal end, and a distal passageway extending from the inner lumen through the distal member to the distal end, wherein the proximal member and distal member are configured for connection with one another, and
an insulating member at least partially separating the distal passageway from the distal member, wherein the insulating member has a lower thermal conductivity than the distal member.

19. The electrode assembly of claim 18, including a temperature sensor in the distal member.

20. The electrode assembly of claim 18, wherein the proximal member is comprised of an electrically nonconductive material and the distal member is comprised of an electrically conductive material.

21. The electrode assembly of claim 18, wherein the diameter of the inner lumen is greater than the diameter of the distal passageway and are connected together by a tapered transition portion of the inner lumen.

22. The electrode assembly of claim 18, wherein the insulating member is integrally formed with the proximal member as a portion of the proximal member which extends through the distal passageway of the distal member.

23. The electrode assembly of claim 18, wherein the inner lumen includes a hydrophilic coating.

24. An irrigated ablation electrode assembly comprising:
a proximal member having an outer surface, an inner lumen and a proximal passageway extending from the inner lumen to the outer surface of the proximal member, the inner lumen including a hydrophilic coating; and a distal member having an outer surface, a distal end, and a distal passageway extending from the inner lumen through the distal member to the distal end;

wherein the proximal member and distal member are configured for connection with one another.

25. The electrode assembly of claim 24, wherein the diameter of the inner lumen is greater than the diameter of the distal passageway and are connected together by a tapered transition portion of the inner lumen.

* * * * *

UNITED STATES PATENT AND TRADEMARK OFFICE
CERTIFICATE OF CORRECTION

PATENT NO. : 8,551,085 B2  Page 1 of 1
APPLICATION NO. : 12/440866
DATED : October 8, 2013
INVENTOR(S) : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1247 days.

Signed and Sealed this
Fifteenth Day of September, 2015

Michelle K. Lee
*Director of the United States Patent and Trademark Office*